United States Patent [19]

Cox et al.

[11] Patent Number: 5,168,052
[45] Date of Patent: Dec. 1, 1992

[54] METHOD FOR PRODUCING 20-DEOXOTYLOSIN

[75] Inventors: Karen L. Cox, Martinsville; Eugene T. Seno, Indianapolis, both of Ind.

[73] Assignee: Eli Lilly and Company, Indianapolis, Ind.

[21] Appl. No.: 497,158

[22] Filed: Mar. 20, 1990

Related U.S. Application Data

[63] Continuation-in-part of Ser. No. 173,907, Mar. 28, 1988, abandoned.

[30] Foreign Application Priority Data

Mar. 22, 1989 [EP] European Pat. Off. ........ 89302837.3

[51] Int. Cl.$^5$ .................. C12P 19/00; C12N 1/21; C12N 15/52; C12N 15/76
[52] U.S. Cl. .................. 435/72; 435/69.1; 435/71.1; 435/91; 435/169; 435/172.1; 435/172.3; 435/252.35; 435/320.1; 435/886; 536/7.1; 536/27; 935/6; 935/14; 935/22; 935/29; 935/38; 935/39; 935/40; 935/42; 935/59; 935/60; 935/61; 935/75
[58] Field of Search .................. 536/7.1, 27; 435/72, 435/69.1, 71.1, 91, 169, 172.1, 172.3, 252.35, 320.1, 886; 935/6, 14, 22, 29, 38, 39, 40, 42, 59, 60, 61, 75

[56] References Cited

U.S. PATENT DOCUMENTS 4,345,069  8/1982  Sakakibara et al. .................. 536/7.1

OTHER PUBLICATIONS

Chater et al., 1985, The EMBO J. 4:1893-1897.
Nature, 314:642-644 (1985) Hopwood, et al.
Nature, 309:462-464 (1984) Malpartida and Hopwood.
Antimicrobial Agents and Chemotherapy 20:214-225 (1981) Baltz and Seno.
In Protein Engineering 365 Inouye and Sarma ed., Academic Press, Inc. Baltz, et al. (1986).
Journal of Antibiotics 36:131 (1982) Baltz, et al.
Journal of Natural Products 49:971 (1986) Cox, et al.
Proc. Natl. Acad. Sci. USA 84:8248 (1987) Fishman, et al.

Primary Examiner—Richard C. Peet
Attorney, Agent, or Firm—William B. Scanlon; Leroy Whitaker

[57] ABSTRACT

The present invention, utilizing recombinant DNA technology, provides a novel method for obtaining 20-deoxotylosin from a tylosin producing microorganism. 20-deoxotylosin is useful as an antibiotic with a microbial inhibitory activity similar to tylosin.

9 Claims, 4 Drawing Sheets

METHOD FOR PRODUCING 20-DEOXOTYLOSIN

CROSS-REFERENCE

This application is a continuation-in-part of co-pending U.S. application Ser. No. 07/173,907, now abandoned, filed Mar. 28, 1988.

BRIEF SUMMARY OF THE INVENTION

The present invention provides a new method for producing 20-deoxotylosin. The method involves the transformation of a mutant microorganism containing defective tylosin biosynthetic genes. The nearly exclusive production of 20-deoxotylosin may be obtained by transforming a mutant microorganism, one that prior to the mutations could produce tylosin, with a DNA sequence that complements a defective gene in the tylosin biosynthetic pathway. The invention further comprises recombinant DNA expression vectors and transformed microorganisms.

The present invention, utilizing recombinant DNA technology, discloses a method for obtaining 20-deoxotylosin, a compound not previously obtainable from a microorganism. Transforming a mutant microorganism containing a defective tylosin biosynthetic pathway such that the resultant transformant contains, in effect, a single tylI mutation allows for the nearly exclusive production of 20-deoxotylosin. A tylI mutation in the tylosin biosynthetic pathway prevents the oxidation of the C-20 methyl group on the tylosin lactone ring, ultimately resulting in a product having a structure identical to tylosin except that the C-20 methyl group on the lactone ring is not oxidized. 20-Deoxotylosin is biologically active and has the potential to be modified into other useful medicines.

Until now, the development and exploitation of recombinant DNA technology in antibiotic producing organisms has been directed mainly toward the development of cloning vectors for the ultimate production of novel antibiotics. A previous method for obtaining novel antibiotics is mutasynthesis, the feeding of unnatural side chain precursors to an idiotroph genetically blocked in antibiotic biosynthesis. Another method is hybrid biosynthesis in which a wild-type strain is fed an unnatural precursor in the presence of an enzyme inhibitor which phenotypically blocks the biosynthetic pathway of the recipient strain. Protoplast fusion has also been used and is a good method for the interspecific transfer of genetic backgrounds.

While certain hybrid antibiotics have been discussed by Hopwood et al., *Nature* 314 642 (1985), the present invention concerns the effective utilization of mutants blocked in the tylosin biosynthetic pathway and not the transfer of biosynthetic genes between Streptomyces species producing different antibiotics. Improved vectors for use in antibiotic-producing organisms were disclosed also in Malpartida and D. A. Hopwood, *Nature* 309:462 (1984). The present invention, however, is primarily concerned with the tylosin biosynthetic pathway and cloning of genes in the tylosin biosynthetic pathway. The application of recombinant DNA technology to an antibiotic biosynthetic pathway was recently described in European Publication, EP A 0 238 323, published Sep. 23, 1987, and is disclosed also in continuation-in-part application U.S. Ser. No. 07/351,350, filed May 12, 1989, herein incorporated by reference. That application discloses vectors and methods for increasing the antibiotic-producing ability of an antibiotic-producing organism. The method involves providing of an enzyme or other gene product that is rate-limiting in an antibiotic biosynthetic pathway. In contrast, the present invention concerns a new method for producing 20-deoxotylosin, a compound not previously obtainable from a microorganism. Such production can now be obtained by transforming a microorganism with a recombinant DNA vector containing genes that complement defective genes in the microorganism's tylosin biosynthetic pathway.

By utilizing such a microorganism, both the complexity and cost of producing 20-deoxotylosin is reduced. While 20-deoxotylosin has been made chemically by a complex reduction of tylosin, the reduction of tylosin to 20-deoxotylosin is both inefficient and costly. Production of complex molecules, such as 20-deoxotylosin, by fermentation is more efficient and cost effective than direct chemical synthesis. In addition, known fermentation and purification procedures can be used, so a minimum level of development effort is needed for commercial exploitation. The present invention is particularly significant in that it allows for the further application of recombinant DNA technology to Streptomyces. Because over two-thirds of the known natural antibiotics are produced by Streptomyces, it is especially desirable to develop methods that are applicable to that industrially important group.

For purposes of the present invention, the following terms are defined below.

Antibiotic-Resistance-Conferring Gene—a DNA segment that encodes an activity that confers resistance to an antibiotic.

Recombinant DNA Cloning Vector—any selectable and autonomously replicating or chromosomally integrating agent, including but not limited to plasmids and phages, comprising a DNA molecule to which additional DNA can be or has been added.

rep—as used in the Figures, a plasmid origin of replication.

Restriction Fragment—any linear DNA generated by the action of one or more restriction enzymes.

Transformant—a recipient host cell, including the viable protoplast thereof, that has undergone transformation.

Transformation—the introduction of DNA into a recipient host cell,—including the viable protoplast thereof, that changes the genotype of the recipient cell.

Tylosin Biosynthetic Gene—a DNA segment that encodes an enzymatic activity, or encodes a product that regulates expression of an enzymatic activity, that is necessary for an enzymatic reaction in the process of converting primary metabolites to antibiotic intermediates, which can also possess antibiotic activity, and then on to the final product, tylosin.

Blocked Mutant—an organism that produces little or no tylosin because of a mutational defect, including but not limited to a deletion, in one or more tylosin biosynthetic genes.

Complement—to eliminate a genetic deficiency caused by a mutation in a tylosin biosynthetic gene in a microorganism by providing such organism with a DNA sequence which 1) comprises a wild type allele of such gene, or 2) restores the wild type phenotype of such gene.

Tylosin Biosynthetic Pathway—the entire set of tylosin biosynthetic genes and biochemical reactions necessary for the process of converting primary metabolites to antibiotic intermediates and then to tylosin.

DESCRIPTION OF THE FIGURES

To aid the understanding of the reader, the following is a brief description of the drawings.

Figure 1A:
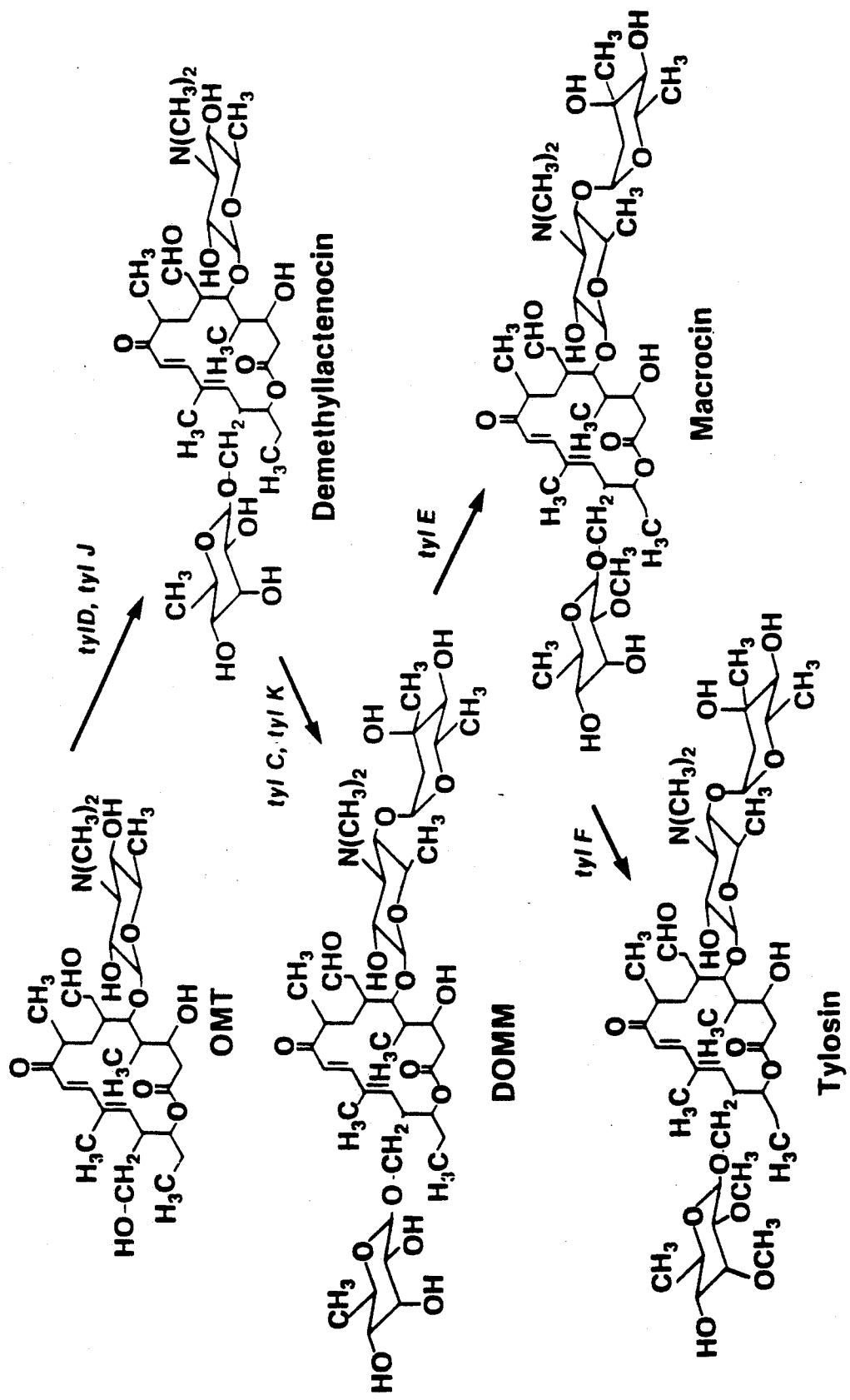
FIG. 1: The Tylosin Biosynthetic Pathway from Tylactone to Tylosin
Figure 2:
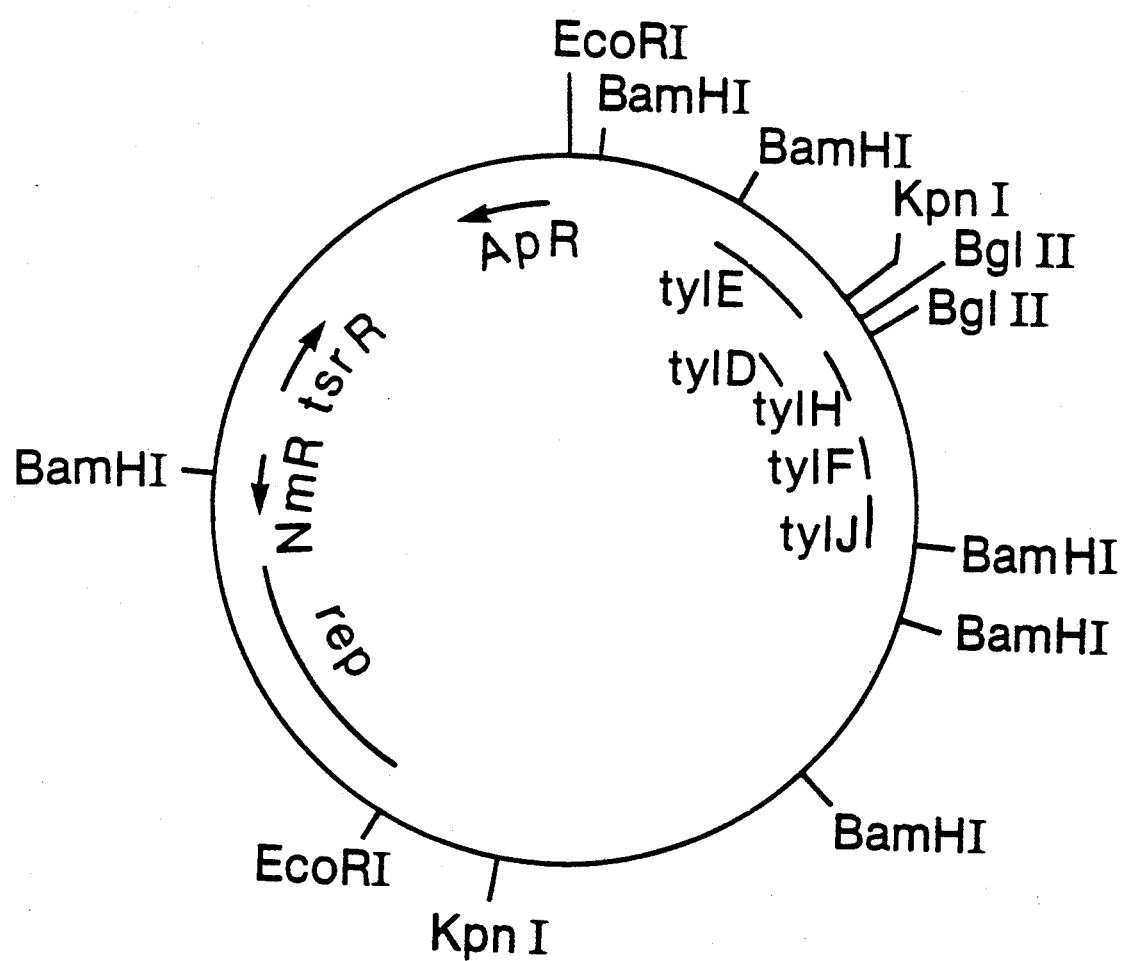
FIG. 2: Restriction Site and Function Map of Plasmid pHJL280.

In the restriction site maps, for convenience, not all cut sites of a given restriction enzyme are shown. The location of individual genes, schematically represented by line segments on the maps, was determined by deletion mapping and only approximates the location of a given gene.

DETAILED DESCRIPTION OF THE INVENTION

In accordance with the invention, there is provided a process for producing 20-deoxotylosin which comprises culturing a tylosin-producing strain of Streptomyces, said strain:

(a) Comprising one or more mutations that prevent the expression of tylosin biosynthetic genes tYlI and R, in which R is one or more tylosin biosynthetic genes selected from tylA, tylB, tylL, tylM, tylH, tylD, tylJ, tylG, tylK, tylC, tylE, or tylF; and, (b) being transformed with a recombinant DNA cloning vector which comprises DNA which complements said mutation or mutations in R thereby allowing for the expression of R; said culture conditions suitable for cell growth, expression of R and production of 20-deoxotylosin.

Also provided are recombinant DNA cloning vectors and 20-deoxotylosin producing microorganisms transformed with the aforementioned genes and vectors useful in the invention. The 20-deoxotylosin compound produced by the present invention is useful due to its antimicrobial activity.

The present invention is best constructed by transforming Streptomyces fradiae GS77 with plasmid pHJL280. Streptomyces fradiae GS77 (also alternately named A252.8) is a blocked mutant which fails to produce tylosin because of mutations in the tylD and tylI biosynthetic genes. The tylD mutation prevents the biosynthesis or attachment of the mycinose precursor (6-deoxy-D-allose) to the tylosin lactone. The tylI mutation blocks the oxidation of the C-20 methyl group on the lactone ring. Thus, *S. fradiae* GS77 makes an altered form of tylosin which lacks mycinose and is not oxidized at the C-20 position. Absent the present invention, the major tylosin-like macrolide antibiotics produced by *S. fradiae* GS77 are 20-deoxy-20-dihydro-O-mycaminosyl tylonolide and 20-deoxy-20-dihydrodemycinosyl tylosin.

The *Streptomyces fradiae* GS77 strain was constructed by N-methyl-N'-nitro-N-nitrosoguanidine (MNNG) mutagenesis of *S. fradiae* GS48 (NRRL 12170), a strain having a mutation in the tylD biosynthetic gene. Treatment of *S. fradiae* GS48 with MNNG, in substantial accordance with the mutagenesis procedure of Baltz and Seno (1981) in Antimicrobial Agents and Chemotherapy 20:214–225, resulted in the generation of the desired *S. fradiae* GS77 blocked mutant strain. The *Streptomyces fradiae* GS77 strain is a double blocked mutant containing not only the tylD mutation, but also a newly induced mutation in the tylI gene. *Streptomyces fradiae* GS77 (alternately designated A252.8) has been deposited (Oct. 16, 1980), under the terms of the Budapest Treaty, and can be obtained from the American Type Culture Collection (ATCC), Rockville, Md. 20852, under the accession number ATCC 31733.

Plasmid pHJL280, a vector useful in the present invention, comprises the wild-type tylD biosynthetic gene but not the tylI gene. Therefore, transformation of *Streptomyces fradiae* GS77 with plasmid pHJL280 results in genetic complementation of the tylD mutation and, because of the presence of the wild-type gene, expression of the tylD gene product. The only mutational block in the tylosin biosynthetic pathway which remains after transformation with pHJL280, namely a block at the step requiring the tylI gene, prevents oxidation at the tylosin C-20 position. With this type of blockage, nearly exclusive production of 20-deoxotylosin is obtained in high yield. Plasmid pHJL280 can be obtained from *E. coli* K12 HB101/pHJL280, a strain deposited under the terms of the Budapest Treaty on Feb. 18, 1986, and made part of the permanent stock culture collection of the Northern Regional Research Laboratory (NRRL), Peoria, Ill. 61604. It is available as a stock reservoir of the plasmid under the accession number NRRL B-18043.

Figure 3:
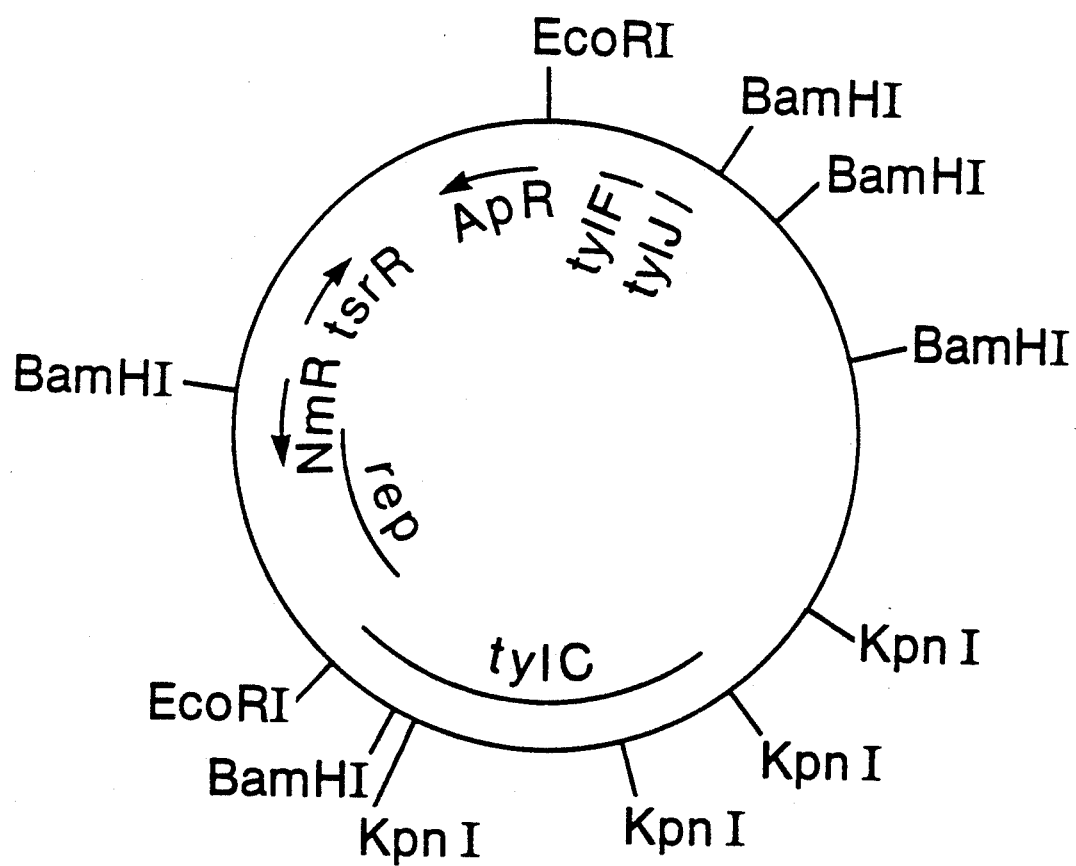
FIG. 3: Structures of Tylosin and 20-Deoxotylosin

To better appreciate the present invention, one must understand how tylosin is biosynthesized in tylosin-producing microorganisms. Tylosin is composed of a 16-member branched lactone (tylonolide) to which three sugars (mycarose, mycaminose, and mycinose) are attached. The lactone is derived from two acetates, five propionates, and a butyrate by condensation of a propionyl-S-coenzyme A molecule with two malonyl-S-coenzyme A molecules, four methylmalonyl-S-coenzyme A molecules, and an ethylmalonyl-S-coenzyme A molecule by a scheme believed analogous to that involved in fatty acid biosynthesis. This process requires the product of the tylG gene. Lactone formation, sugar biosynthesis/attachment, and the conversion of resultant intermediate compounds to tylosin are catalyzed by a series of gene-encoded enzymes. The cloning and/or mutating of genes that code for such enzymes allows for the manipulation of this biosynthetic pathway. A comparison of the structures of tylosin and 20-deoxotylosin is depicted in FIG. 3 of the accompanying drawings.

Analysis shows that tylosin is assembled by a series of biosynthetic steps. Studies have shown that tylactone, the first intermediate excreted by *Streptomyces fradiae*, is converted to tylosin by a preferred sequence of reactions which include: (1) addition of mycaminose to the C-5 hydroxyl position of the lactone; (2) oxidation of the C-20 methyl group to form a hydroxymethyl group; (3) dehydrogenation of the C-20 hydroxymethyl group to form a formyl group; (4) oxidation of the C-23 methyl group to produce a hydroxymethyl group; (5) addition of 6-deoxy-D-allose to the C-23 hydroxymethyl group; (6) addition of mycarose to the 4'-hydroxyl group of mycaminose; (7) addition of a methyl group to the 2'''-hydroxyl position of demethylmacrocin (DOMM), and (8) addition of a methyl group to the 3'''-hydroxyl position of macrocin to produce tylosin. Genes that are required for the preferred sequence of reactions converting tylactone to tylosin include, but are not limited to, tylA, tylB, tylL, tylM, tylI, tylH, tylD, tylJ, tylK, tylC, tylE, and tylF. A schematic representation of the tylosin biosynthetic pathway is presented in FIG. 1 of the accompanying drawings. Each arrow in FIG. 1 represents a conversion step requiring the biosynthetic gene products indicated by the gene name(s) located above the corresponding arrow.

As previously described, the method of the present invention utilizes tylosin biosynthetic genes to complement mutations in certain genes of the tylosin biosynthetic pathway. Various methods for isolating antibiotic biosynthetic genes are now well known in the art. For instance, Example 1 below is a preferred method for isolating Streptomyces chromosomal and plasmid DNA which is generally applicable to all antibiotic-producing organisms. After chromosomal or plasmid DNA is isolated from a particular antibiotic-producing organism, a genomic library of the prepared DNA can be constructed in accordance with methods that are also well known in the art. For purposes of illustration, Example 2 discloses a preferred method for preparing a genomic library that increases the likelihood that an entire antibiotic biosynthetic pathway will be cloned. After the genomic library is constructed, DNA fragments containing antibiotic biosynthetic genes can be identified by a number of methods. For example, a DNA probe can be constructed based on the knowledge of at least part of the amino acid sequence of an antibiotic biosynthetic enzyme. This probe can then be hybridized to the library by standard procedures to detect DNA fragments containing the gene which codes for the enzyme. Another method is to introduce the cloned DNA fragments into mutants blocked in antibiotic biosynthesis, and screen for restoration of antibiotic production. Depending upon the vector in which the library was prepared, the DNA may be directly transformed into the mutants, or first subcloned into an appropriate vector using standard procedures.

Those skilled in the art will recognize that the present invention is not limited to the production of 20-deoxotylosin in *Streptomyces fradiae*. For example, *Streptomyces rimosus* and *Streptomyces hygroscopicus* are two other microorganisms that naturally produce tylosin by virtue of a tylosin biosynthetic pathway. Therefore, both of these microorganisms may also be used for purposes of the present invention. Upon inducing mutations that result in gene deficiencies in combination with at least a tylI mutation, these organisms can be used as hosts for purposes of the present invention. Thus, any tylosin producing strain containing the tylI mutation in combination with any other tyl mutation can be converted to a 20-deoxotylosin producer by introducing the wild type tyl genes for all of the mutant tyl genes, except for tylI.

Moreover, as one skilled in the art will appreciate, a tylI mutation(s), alone, might be expected to lead to the production of 20-deoxotylosin without the need for any transformation with complementing sequences. One method for generating such a 20-deoxotylosin-producing strain is to treat a tylosin-producing strain such as, for example, *Streptomyces fradiae*, with a chemical mutagen and then screen the population for mutants which contain only a tylI mutation. Such tylI mutants would be easily recognized by their production of the desired 20-deoxotylosin. Example 14 contains a protocol for obtaining a tylI mutation(s). Thus, also encompassed by the invention is the equivalent use of a 20-deoxotylosin producing Streptomyces mutant containing only the tylI mutation(s).

Alternative methods for transforming microorganisms for purposes of the present invention include classical methods of genetic recombination such as, for example, protoplast fusion, conjugation and transduction. Any of these methods could be used to introduce normal tyl genes into the mutant background. In addition, those skilled in the art will recognize that the present invention is not limited to the use of plasmid pHJL280 or any other particular vector. Any vector, like a bacteriophage or plasmid, capable of replication and maintenance or integration in *Streptomyces fradiae*, *Streptomyces rimosus*, *Streptomyces hygroscopicus* or any other tylosin producing organism can be modified to carry the appropriate tylosin biosynthetic genes and then used in accordance with the present invention. Such vectors into which tylosin biosynthetic genes can be ligated include, but are not limited to, plasmids pIJ702, pIJ903, pIJ922, and pIJ941. Plasmid pIJ702 can be obtained from the American Type Culture Collection, Rockville, Md., 20852, under the accession number ATCC 39155. Plasmids pIJ903, pIJ922, and pIJ941 can be obtained from the John Innes Streptomyces Culture Collection, John Innes Institute, Colney Lane, Norwich, England NR4 7UH, under the respective accession numbers 3417, 3419, and 3338. Plasmids pHJL280, pHJL284, pHJL309, pHJL311, pHJL315, pSET551, pSET552, pSET555, and pSET556 contain various tylosin biosynthetic genes and are on deposit at the Northern Regional Research Laboratory (NRRL), Agricultural Research Service, U.S. Department of Agriculture, Peoria, Ill. 61604, with the respective accession numbers, B-18043, B-18044, B-18045, B-18046, B-18047, B-18411, B-18412, B-18413, and B-18414. These vectors replicate in *S. fradiae* and can be made to replicate in the other tylosin-producing species and are thus useful in the present method for producing 20-deoxotylosin. Table 1 provides a brief description of several plasmids used to exemplify the method of the present invention.

TABLE 1

| Plasmids Comprising Tylosin Biosynthetic Genes | | | |
|---|---|---|---|
| Host/Designation | Tylosin Gene(s) | NRRL Accession No. | Deposit Date |
| *E. coli* K12 HB101/pHJL280 | D,E,F,H,J | B-18043 | Feb. 18, 1986 |
| *E. coli* K12 HB101/pHJL284 | C,F,J | B-18044 | Feb. 18, 1986 |
| *E. coli* K12 HB101/pHJL309 | L,M | B-18045 | Feb. 18, 1986 |
| *E. coli* K12 HB101/pHJL311 | C,F,J,K,H | B-18046 | Feb. 18, 1986 |
| *E. coli* K12 JM109/pHJL315 | D,E,F,H,J | B-18047 | Feb. 18, 1986 |
| *E. coli* K12 DH5α/pSET551 | G,I | B-18411 | Sept. 14, 1988 |
| *E. coli* K12 DH5α/pSET552 | I,A,B | B-18412 | Sept. 14, 1988 |
| *E. coli* K12 DH5α/pSET555 | G,I,A,B | B-18413 | Sept. 14, 1988 |
| *E. coli* K12 DH5α/pSET556 | G,I,A,B | B-18414 | Sept. 14, 1988 |

As previously indicated, transformation of *Streptomyces fradiae* GS77 with plasmid pHJL280, which contains the wild-type tylD gene but not the tylI gene, results in the nearly exclusive production of 20-deoxotylosin. When the tylD gene is introduced into *S. fradiae* GS77, by transformation with plasmid pHJL280, the effects of the tylD mutation are eliminated because the wild type tylD gene is now present, and the tylD gene product is now capable of being expressed. Therefore, the only defect in the transformed S. fradiae GS77 strain is the tylI mutation which prevents oxidation of the C-20 position on the tylosin lactone ring. With oxidation at the C-20 position being blocked, nearly exclusive production of 20-deoxotylosin is obtained. Thus, S. fradiae GS77/pHJL280 is a particularly preferred strain for purposes of the present invention.

Plasmid pHJL280 is introduced into Streptomyces fradiae GS77 by protoplast transformation. Plasmid pHJL280 carries an antibiotic resistance conferring gene (resistance to thiostrepton to which S. fradiae GS77 is sensitive), thereby allowing transformants to be selected by regenerating the protoplasts in the presence of thiostrepton. After an appropriate transformant has been identified, it is propagated only in the presence of thiostrepton to maintain the plasmid. To produce 20-deoxotylosin, the transformant is grown under demycinosyltylosin fermentation conditions which have been previously described in U.S. Pat. No. 4,419,447, which is incorporated by reference. The fermentation broth is filtered and the 20-deoxotylosin is extracted, dissolved and crystallized as described for demycinosyltylosin in U.S. Pat. No. 4,419,447. Further details of the transformation, culture, and fermentation procedures are found in the Examples as later presented. 20-Deoxotylosin has a spectrum of activity which is substantially equivalent to tylosin. Thus, 20-deoxotylosin has inhibitory action against the growth of various microbial organisms including both gram-positive and gram negative bacteria and certain microbial plant pathogens. However, the majority of microorganisms against which it has inhibitory action are gram-positive. 20-Deoxotylosin, like tylosin, is well tolerated in animals and effective by both the oral and subcutaneous routes. In addition, past experience has indicated that 20-deoxotylosin will have increased oral absorption and/or increased biostability. Not only is 20-deoxotylosin useful as an antimicrobial compound by itself, it is also useful for making additional tylosin derivatives which also evidence biological activity.

The following non-limiting Examples are provided to further illustrate the invention.

EXAMPLE 1

DNA Isolations for Streptomyces

A. Culture of Streptomyces fradiae

A 48-hour culture of Streptomyces fradiae was grown at 30° C. in 10 ml. of trypticase soy broth (TSB*) by inoculating a single colony into 10 ml. of broth and homogenizing this solution three times until the colony is disrupted. The 10 ml. culture was homogenized and used to inoculate a flask containing 500 ml. of TSB supplemented with glycine to a final concentration of 0.4%. The culture was grown for 48 hours at 30° C. and the mycelia collected by centrifugation at 10,000 rpm for 15 minutes in Sorvall centrifuge bottles using a RC-5 Sorvall and a GSA rotor. About 50 grams of wet mycelia were produced.

Trypticase soy broth is obtained from Baltimore Biological Laboratories, P.O. Box 2431 Cockeysville, Md. 21031 or Difco Laboratories, Detroit, Mich.

The cell pellet was resuspended in 500 ml. of Tris-sucrose (10mM Tris-HCl pH 8.0/1.0mM EDTA/25% sucrose). Next, the suspension was supplemented with 250 ml. of 0.25M EDTA (pH 8.0) and 250 ml. of lysozyme solution [10 mg./ml. lysozyme (Calbiochem) in Tris-sucrose solution]. This mixture was incubated at room temperature for 15 minutes and then 50 mg. of proteinase K (Beckman) was added and the suspension incubated for an additional 30 minutes. About 50 ml. of a 20% w/v solution of sodium dodecyl sulfate (ultrapure obtained from Gallard-Schlesinger Chemical Mfg. Corp., 584 Mineola Place, New York City, N.Y. 11514) was added, gently mixed, and then the lysed cells were incubated at 55° C. for 30 minutes. After 250 ml. of 5M NaCl was gently mixed into the lysed cell solution, the suspension was transferred to Sorvall centrifuge tubes (~ 40 ml./tube) and placed on ice for 2 hours. The solution was centrifuged at 15,000 rpm for 20 minutes in a Sorvall SS34 rotor and centrifuge. The supernatants were pooled together (~ 700 ml.) and 0.64 volume of isopropyl alcohol was added and mixed gently. This solution was transferred to Sorvall centrifuge bottles and the precipitates collected by centrifugation at 10,000 rpm in a Sorvall GSA rotor and centrifuge. The precipitates were air dried and then gently resuspended in TE to a final volume of 100 ml.

About 5.0 mg. of RNAase A (obtained from Sigma, St. Louis, Miss.) was suspended in 1 ml. TE (10mM Tris-HCl pH 8.0/1.0mM EDTA), boiled for two minutes, added to the above DNA suspension together with 5.0 mg of proteinase K and then the mixture was incubated at 4° C. for 15 hours. Next, an equal volume of buffer saturated phenol was added to the mixture and the phases separated by centrifugation (5,000 rpm, GSA rotor, 10 minutes). The aqueous layer was decanted into a 250 ml. graduated cylinder and adjusted to 0.3M NaOAc by the addition of 3M NaOAC (pH 8.0). This solution was placed on ice and 2 volumes of cold ethanol was gently added to avoid mixing the two liquids. Using a procedure developed by Marmur et al., 1961, J. Mol. Biol. 3:208–218, the high molecular weight DNA species were collected by gently swirling a glass rod at the interface between the DNA and ethanol. The thus collected DNA was washed once in 70% ethanol and air dried prior to resuspension in 5 ml. TE (supplemented to 0.1 M NaCl) to a final concentration of 1.4 mg./ml.

EXAMPLE 2

Preparation of Lambda Charon 4 DNA

A. Preparation of Lambda Charon 4 Vector

An overnight culture of Escherichia coli K12 C600$R_k^-M_k^-$(ATCC 33525) was grown at 37° C. in 10 ml. of T broth (10 gm. Bacto-Tryptone, 5 gm. yeast extract, 5 gm. NaCl and distilled water to 1 liter, pH 7.0) supplemented with maltose (20% maltose to 0.2%) and MgSO$_4$ (1M MgSO$_4$ to 10mM). Supplemented broth is designated TMM. A phage stock of Charon 4, ATCC 40432, a standard E. coli K12 lambda cloning vector was serially diluted and 0.1 ml. of the individual phage dilutions were added to 0.1 ml. of a 1/10 dilution of the E. coli culture grown in TMM. These cultures were then incubated at 37° C. for 20 minutes. After 3 ml. of TM top agar (T broth plus 10mM MgSO$_4$ and 0.7% agar) were added, the cultures were plated on T agar (T broth+1.5% agar) supplemented with 10mM MgSO$_4$ and incubated at 37° C. for 16–24 hours. A plate containing ~ 20,000 pfu (plaque-forming units) was selected and flooded with 5 ml. of lambda buffer (6.35 gm. Tris-HCl, 1.18 gm. Tris base, 2.46 gm. MgSO$_4$.7H$_2$O, 5.84 gm. NaCl and distilled water to 1 liter). The plate was scraped into a 50 ml. Sorvall tube and after the addition of 0.1 ml. CHCl$_3$, the tube was centrifuged at 4,000 rpm for 10 minutes. The supernatant was collected in a fresh tube and 0.5 ml. CHCl₃ was added. It should be noted that 3-5 lysates may be made to obtain the proper titer.

B. Preparation of Phage Lysate

A 20 ml. culture of *E. coli* K12 C600R$_k$⁻M$_k$⁻(ATCC 33525) was grown in TMM broth at 37° C. for 16-24 hours. This culture was mixed with 10⁹ pfu of Charon 4 (from the plate lysates of Example 2A and titered according to conventional methods) and incubated at 30° C. for 10 minutes without shaking. The incubated mixture was divided in half and each half was added to a 1 liter flask containing 500 ml. of T broth supplemented with 1M MgSO₄ to a final concentration of 10mM MgSO₄ and shaken at 37° C. until lysis (about 3-8 hours).

After lysis, DNAase I [(10 mg./ml. in 50mM Tris-HCl, pH 8.0), obtained from Worthington Diagnostic, Freehold, N.J. 07728] was added to a final concentration of 1 µg./ml. per flask and the flasks were shaken for 15 minutes. Next, 7.9 gm. NaCl/100 ml. was added to each flask and shaken into solution. After 0.2 ml. of chloroform was added per flask, the contents were transferred to Sorvall centrifuge bottles and spun in a GSA rotor at 4,000 rpm for 10 minutes. After pooling the supernatants, polyethylene glycol 6000 (obtained from Sigma) was added to a final concentration of 100 gm./l., shaken into solution and placed in an ice bath for 1 hour.

Aliquots of this solution were transferred to Sorvall bottles and the precipitates were collected by centrifugation in a GSA rotor for 10 minutes at 6,000 rpm. All pellets were resuspended in a total volume of 15 ml. of lambda buffer and transferred to a 50 ml. Sorvall tube containing 15 ml. of chloroform and vortexed before centrifugation at 4,000 rpm for 10 minutes.

After the upper aqueous phase was collected, cesium chloride (0.814 gm./ml.) was added and adjusted to obtain a refractive index of 1.3809. The solution was transferred to Beckman ultracentrifuge tubes and spun to equilibrium (18 hr., 50,000 rpm). The phage band was extracted with a needle and syringe and dialyzed against 2 liters of lambda buffer for 4-8 hours. After the approximate DNA concentration was determined, lambda DNA was extracted by the addition and gentle mixing of an equal volume of buffer-saturated (50mM Tris-HCl pH 8.0) phenol [Ultra-pure obtained from Bethesda Research Laboratory (BRL) Gaithersburg, Md. 20877]. The phases were separated by centrifugation in a Sorvall centrifuge and the aqueous layer removed and mixed with an equivalent volume of ether. The phases were again separated by centrifugation and the ether layer removed and discarded. After the ether extraction step was repeated, the λ DNA solution was made 0.3M NaOAc by the addition of 3M NaOAc pH 8.0. The DNA was precipitated by the addition of 2 volumes cold ethanol and stored overnight at −20° C. The DNA was collected by centrifugation (15,000 rpm, 15 minutes, Sorvall tubes), washed once with 70% ethanol and air dried. This DNA pellet was resuspended in 500 µl. TE to a final concentration of ∼ 400 µg./ml.

C. Preparation of Charon 4 EcoRI Arms

To obtain both the left and right arms of Charon 4, 250 µl. of Charon 4 DNA (100 µg.), 30 µl. 10X EcoRI buffer (1000mM Tris-HCl pH 7.5, 500mM NaCl, and 50mM MgCl₂), 30 µl. 1 mg./ml. bovine serum albumin (BSA), and 10 µl. distilled water were digested with 10 µl. [(100 units) New England Biolabs, Inc., 32 Tozer Road, Beverly, Ma. 01915] EcoRI enzyme for 2 hours at 37° C. An additional 10 µl. of EcoRI enzyme was added and incubated for another hour. The reaction was terminated by increasing the temperature to 70° C. for 10 minutes. An equal volume of buffer saturated phenol was mixed in and the phases separated by centrifugation in a microfuge. The aqueous layer was removed and extracted twice with ether as described in the preceding example.

The DNA suspension was divided in half and added to two SW40 tubes containing 10-40% w/v sucrose (in 1M NaCl, 20mM Tris-HCl pH 8.0, and 5mM EDTA) gradients containing 2 µg./µl. ethidium bromide essentially as described in Maniatis et al., 1982, Molecular Cloning, Cold Spring Harbor Laboratory, Cold Spring Harbor, N.Y. After running in a Beckman SW40 rotor for 15 hours at 25,000 rpm at 5° C., the bands were visualized by UV light and the four visible bands extracted with a syringe and needles. The ethidium bromide was extracted with n-butanol and the resulting DNA examined by agarose gel electrophoresis (AGE). The two bands representing the left and right arms of Charon 4 were mixed equimolar, diluted in half, precipitated by the addition of two volumes of ethanol and stored at −20° C. overnight. The DNA precipitate was collected by centrifugation in an HB4 rotor (Sorvall tube, 12,000 rpm, 30 minutes) and then resuspended in 100 µl. TE to a final concentration of 0.174 µg./µl. Charon 4 arm DNA.

EXAMPLE 3

Preparation of *Streptomyces fradiae* DNA

A. Culture of *Streptomyces fradiae* and Preparation of DNA Suspension

A culture of *Streptomyces fradiae* was grown under conditions and DNA prepared in substantial conformance with Example 1.

B. Collection of High Molecular Weight Fractions

Approximately one-half ml. of the DNA suspension from part A above was layered onto the top of four SW40 Beckman polyallomer tubes containing a 5-20% w/v sucrose gradient made in substantial accordance with the teaching of Example 2C with the exclusion of ethidium bromide and the substitution of 5% w/v and 20% w/v sucrose solutions for the respective 10% w/v and 40% w/v sucrose solutions. These gradients were run for 17 hours at 30,000 rpm using a Beckman SW40 rotor in a Beckman ultracentrifuge. One-half ml. fractions were collected from each tube by puncturing the bottom of the tube and collecting the drops. The fractions were examined by AGE (agarose gel electrophoresis)and the high molecular weight fractions (>50 kb) were pooled and precipitated by conventional methods. The DNA precipitate was resuspended in 500 µl. TE to a final concentration of 1.4 µg./µl.

C. Preparation of the *Streptomyces fradiae* Insert DNA

About 0.5 ml. of the DNA from the preceding example was adjusted to 0.3M NaOAc by the addition of 3M NaOAc and precipitated with 2 volumes cold ethanol and stored at −20° C. overnight. The precipitate was collected by centrifugation, washed in ethanol and resuspended in 1.6 ml. TE to a final concentration of 0.46 µg./µl. and held at 4° C. for 16 hours. Three reactions were set up to digest the DNA with HaeIII restriction enzyme and three reactions were set up to digest the DNA with AluI restriction enzyme.

1. HaeIII Restriction Enzyme Digestions

The HaeIII reaction mixture was set up containing about 540 µl. of the suspended DNA, 250 µl. 10X HaeIII buffer (500mM NaCl, 60mM MgCl₂, 60mM β-mercaptoethanol), 1700 µl. water, and 8.9 µl. of a 1/10 dilution of HaeIII enzyme (7 units/µl. BRL) in 1X HaeIII buffer. Three reactions, each containing ~ 800 µl., were prepared from the single HaeIII reaction mixture and incubated at 37° C. for 20 minutes, 40 minutes, and 60 minutes and then placed on ice. The extent of digestion was monitored by AGE. To each reaction, 2 µl. of a 1/10 dilution of HaeIII restriction enzyme was added and incubation for 30 minutes at 37° C. continued. The reactions were again placed on ice and the extent of digestion was monitored by AGE. This 2 µl. enzyme addition was repeated, and the extent of the final digestion was monitored by AGE. The three reactions were pooled together, made 0.3M NaOAc by the addition of 3M NaOAc, rinsed with 2 volumes ethanol and precipitated overnight at −20° C.

2. AluI Restriction Enzyme Digestions

The same procedure with respect to the HaeIII digestions was used for a similar digestion with AluI except that 10 µl. of a 1/10 dilution of AluI (6 units/µl. BRL), ~ 1700 µl. of distilled water and 10X AluI buffer (500mM Tris-HCl pH 8.0, 50mM MgCl₂, 500mM NaCl, and 10mM dithiothreitol) were used in place of the HaeIII reaction enzyme and buffer. The three reactions were run in substantial accordance with the teaching of the HaeIII digestions with the exception that only one additional incubation period with AluI enzyme was required. These reactions then were pooled and precipitated.

The two DNA digestions were separately collected by centrifugation (12,000 rpm, 12 minutes) in a HB4 rotor. The precipitates were washed once with 70% ethanol. Finally, the precipitates were resuspended separately in 200 µl. TE. The suspensions were pooled, and TE was added to a final volume of 600 µl. About 200 µl. of this pooled DNA was added to each of three, 13 ml. 5–20% w/v sucrose gradients. These three gradients were run for 17 hours in a SW40 Beckman rotor at 30,000 rpm at 5° C. About 30 fractions, containing ~ 0.4 ml. each, were collected from each tube by puncturing the bottoms of the gradient tubes and collecting drops. Each fraction was analyzed on AGE and those corresponding to DNA in the size range of 10–25 kb DNA were pooled and precipitated by conventional methods. The precipitate was resuspended in 800 µl. TE at a concentration of 0.065 µg./µl.

3. Methylation of *Streptomyces fradiae* DNA

About 200 µl. of 5X EcoRI methylase buffer (500mM Tris-HCl pH 8.0, 12.5mM dithiothreitol, 25mM EDTA, 2 mg./ml. BSA, and 5.5 µM S-adenosyl methionine) and 10 µl. EcoRI methylase (10 units/µl. BRL) were added to the ~ 800 µl. of DNA prepared above and then incubated at 37° C. for 2 hours. The DNA was extracted twice with buffer saturated phenol and the phenol was re-extracted with TE. The aqueous phases were pooled and extracted twice with ether and then precipitated with sodium acetate followed by two volumes of ethanol and incubated at −20° C. for 2 hours. The precipitate was collected by centrifugation (12,000 rpm, 15 minutes) and the DNA washed once in 70% ethanol, air dried, and then resuspended in 75 µl. of TE. This contained approximately 44 µg. of methylated AluI-HaeIII partially digested *S. fradiae* DNA.

4. Linker Addition

About 40 µl. of EcoRI linker (pGGAATTCC obtained from Collaborative Research, Inc., 128 Spring Street, Lexington, Ma. 02173) at 100 µg./ml. in TE was incubated at 65° C. for three minutes and then cooled on ice. A ligation reaction containing 70 µl. of methylated *Streptomyces fradiae* DNA, 40 µl. linker DNA, 40 µl. 5X ligase/kinase buffer (250mM Tris-HCl pH 7.8, 25% glycerol, 25mM dithiothreitol, and 50mM MgCl₂), 40 µl. 0.66M ATP and 12 µl. (1 unit/µl. Boehringer-Mannheim Biochemicals) T4 DNA ligase were incubated at room temperature for 12 hours. The reaction was terminated by increasing the temperature to 65° C. for five minutes and then stored at 4° C. 16–24 hours. About 190 µl. of the stored ligation reaction was mixed with 45 µl. 10X EcoRI buffer, 195 µl. distilled water and 20 µl. EcoRI enzyme (10 units/µl. BRL) and incubated at 37° C. for five hours. After the addition of 20 µl. 0.25M EDTA (pH 8.0), the reaction was terminated by increasing the temperatures to 65° C. for five minutes followed by cooling on ice. This reaction was layered onto a 5–30% w/v sucrose gradient and run in a SW40 rotor (18 hours, 30,000 rpm, 5° C.). The tube was punctured at the bottom and 36 five drop fractions were collected. The fractions were examined by AGE and those fractions ranging in size from 10 to 19 kb were pooled, precipitated with sodium acetate and ethanol and stored overnight at −20° C. The DNA precipitates were collected by centrifugation in a Sorvall HB4 rotor (12,000 rpm, 15 minutes), washed once in 70% ethanol, air dried and resuspended in 400 µl. TE. This suspension constitutes the EcoRI linked *S. fradiae* DNA at a concentration of 0.022 µg./µl.

EXAMPLE 4

Production of Phage Library

About 2 µg. of the *Streptomyces fradiae* insert DNA, prepared in Example 3(C), were mixed with 17.2 µl. (~ 3 µg.) Charon 4 arms, prepared in Example 2C, and then the DNA was precipitated by the addition of 3M sodium acetate (to a final concentration of 0.3M NaOAc) and two volumes of ethanol. This mixture was incubated at −70° C. for 15 minutes. The DNA pellet was collected by centrifugation in a Brinkman microfuge for 10 minutes, washed in 70% ethanol and air dried. Next, the pellet was resuspended in 16 µl. of the following ligation reaction mixture: 4 µl. 5X kinase/ligase buffer, 4 µl. 0.66M ATP pH 7.4, 11 µl. distilled water, and 1 µl. T4 DNA ligase; this ligation reaction was incubated at 9° C. for 72 hours.

The ligation was conventionally packaged using Bethesda Research Laboratory packaging extract in substantial accordance with the manufacturer's specification. Other such in vitro packaging mixes, such as, Biotec packaging kit, are available for use in the present application. The packaging mixture was loaded onto a CsCl block gradient and run in a SW50 Beckman rotor (2 hours, 30,000 rpm, 5° C.). The cesium chloride gradients were made in substantial accordance with the teaching of Maniatis et al., 1982, except that the density per 0.5 ml. of CsCl were 1.7, 1.5 and 1.3. The tube was punctured at the bottom and 10-drop fractions were collected and dialyzed individually in a BRL mini-dialysis unit against lambda buffer. The fractions were titered as described in Example 2A using a 10 ml. culture of *E. coli* K12 294 (ATCC 31446) in TMM overnight at 37° C., instead of *E. coli* K12 C600R$_k^-$M$_k^-$, and examined for recombinants. Recombinants were identified by the appearance of non-blue plaques as revealed on T agar plates supplemented with 10mM MgSO$_4$ and 40 μg./ml. 5-bromo-4-chloro-3-indolyl-β-D-galactosidase (X-gal from BRL). The various fractions were pooled to give a library of recombinant phages. Amplification of the primary lysate was made by preparing plate lysates of the library on *E. coli* K12 294 where at least 4,000 recombinant plaques were on each plate. From these plate lysates a large scale phage lysate and DNA prep were done as taught in Example 2. The DNA was resuspended in 1 ml. TE at a concentration of 0.23 μg./μl.

EXAMPLE 5

The Use of a Tylosin-Resistance Gene, tlrB, as a Probe to Detect DNA Sequences Containing Tylosin Biosynthetic Genes in the Lambda Charon 4 Library The amplified phage lysate is plated on *E. coli* K12 294 as described in Example 2A to give about 5,000 plaques per plate and a total of about 20,000 plaques. The plaques are transferred to nitrocellulose filters by the method of Benton and Davis, *Science*, 196:180 (1977) as described in detail in the laboratory manual, *Molecular Cloning* (T. Maniatis, E. F. Fritsch, J. Sambrook, Cold Spring Harbor Laboratory, Cold Spring Harbor, N.Y., 1982, pp. 320-321). The DNA on the filters is hybridized to a radioactive probe consisting of a cloned tylosin-resistance gene, tlrB, in the plasmid pSVB9 (NRRL 18073). The method for the preparation of radioactive DNA probes by "nick translation" is well known to those skilled in the art, and it is described in detail in the text *Molecular Cloning*, pp. 109-112. The method for hybridizing the radioactive probe to the filters is described in detail in *Molecular Cloning*, pp. 324-328.

The phages in plaques which hybridize to the probe are grown to high titer as described in Example 2A, and phage DNA is prepared as described in Example 2B.

EXAMPLE 6

Culture of *E. coli* K12 C600R$_k^-$M$_k^-$/pHJL210 and Isolation of Plasmid pHJL210

A single bacterial colony of *E. coli* K12 C600R$_k^-$M$_k^-$/pHJL210 (NRRL B-15824) was inoculated into LB medium which contains, per liter aqueous solution, 10 gm. Bacto tryptone, 5 gm. Bacto yeast extract and 10 gm. NaCl (pH 7.5) with 25 μg./ml. of ampicillin according to conventional microbiological procedures. The culture was incubated at 37° C. for 16-24 hours. The following morning, 500 ml. of M9 medium (Miller et al., 1979, Experiments in Molecular Genetics, Cold Spring Harbor Laboratories, Cold Spring Harbor, N.Y.) supplemented to 1 mM MgSO$_4$, 0.2% glucose, 0.3-0.4% CAA (casamino acids, Difco), 2 μg./ml. B1 (thiamine-HCl, Sigma) and 25 μg./ml. of ampicillin were inoculated with 5 ml. of the culture. The culture was incubated with vigorous shaking at 37° C. for 16-24 hours and the samples of the culture were inoculated at dilutions of 1/10 to 1/50 into the supplemented M9 media and incubated with vigorous shaking at 37° C. for 2 1/2 to 3 hours. The turbidity of the culture measured with the blue filter was approximately 300 to 400 Klett units. Chloramphenicol (150-175 μg./ml.) was added to the culture and incubation with vigorous shaking was continued for 16-24 hours.

The bacterial cells were harvested by centrifugation at 7500 rpm for 5 minutes at 4° C. and then washed twice with 200 ml. of SV (0.15M NaCl, 0.1M NaEDTA pH 8.0). The pellet was resuspended in 10 ml./gm. wet weight TS solution (25% sucrose, 50mM Tris, pH 8) and placed on ice. To this suspension, 2 ml./gm. wet weight of lysozyme solution (5 mg./ml. in 50mM Tris-HCl pH 7.8) was added and left to chill on ice for 5 minutes. Next, 4 ml./gm. wet weight of 0.25M EDTA pH 8.0 was added and chilled for another 5 minutes. Upon the addition of 16 ml./gm. wet weight lysis solution (0.4% deoxycholate, 1% Brij 58, 50mM Tris and 0.0625M EDTA, pH 8) the mixture was incubated at 37° C. for 15-30 minutes. The debris was removed by centrifugation in a Sorvall SS34 rotor at 21,000 rpm for 15-30 minutes at 4° C. The supernatant was saved and 0.1 vol. of 3M NaOAc, at pH 8 and 0.64 volumes isopropyl alcohol were added to the supernatant. The solution was centrifuged at 10,000 rpm for 10 minutes at 4° C., whereupon the pellet was resuspended in 1 ml of TE (10mM Tris, 1 mM EDTA pH 8). The plasmid DNA was purified by centrifugation to equilibrium in cesium chloride (CsCl) density gradients containing propidium diiodide according to known techniques.

EXAMPLE 7

Subcloning *Streptomyces fradiae* DNA From The Recombinant Bacteriophages Which Hybridized To The Probe A. Digestion of Plasmid pHJL210

About 10 μl. (~11 μg.) of plasmid pHJL210 (prepared in Example 6) was added to 5 μl. 10X EcoRI buffer, 5 μl. BSA, 25 μl. distilled water and 5 μl. of EcoRI restriction enzyme (10 units/μl. NEB) and incubated for two hours at 37° C. The reaction was terminated by raising the temperature to 70° C. for 10 minutes. The DNA was precipitated by addition of 6 μl. 3M NaOAc pH 8.0 and 120 μl. cold ethanol. After incubation at −70° C. for 15 minutes, the DNA was collected by centrifugation in a Brinkman microfuge for 10 minutes. The DNA pellet was washed once with 70% ethanol, air dried and then resuspended in 80 μl. distilled H$_2$O. This suspension was supplemented with 20 μl. 5X CIAP buffer (500mM Tris-HCl pH 7.5, 250mM NaCl and 50mM MgCl$_2$) To dephosphorylate the DNA, 3 μl. of a 1/10 dilution of calf intestinal alkaline phosphatase, Grade III (4 units/μl. Boehringer Mannheim) prepared in accordance with the manufacturer's specification, was added and the reaction incubated first at 37° C. for 30 minutes and then at 70° C. for an additional 30 minutes.

B. Preparation of the *Streptomyces fradiae* DNA Inserts

About 10 μl. (~ 2 μg.) of the DNA from each bacteriophage (prepared in Example 2) was incubated with 2 μl. 10X EcoRI buffer, 2 μl. BSA, 5 μl. water, and 1 μl. EcoRI enzyme (10 units/μl. NEB) for three hours at 37° C. The reaction was terminated by increasing the temperature to 70° C. for 10 minutes.

C. Ligation

About 10 μl. of the dephosphorylated and EcoRI-digested pHJL210 DNA was added to the 20 μl. EcoRI-digested bacteriophage DNA and the mixture precipitated with 3 μl. 3M NaOAc and 82 μl. cold 100% ethanol. After incubation at −70° C. on dry ice for 10 minutes, the precipitate was collected by centrifugation, washed once with 70% ethanol and air dried. The pellet was resuspended in 23 μl. distilled water and to this solution, 8 μl. 0.66M ATP, 8 μl. 5X kinase/ligase buffer and 1 μl. ligase (Boehringer-Mannheim) were added and the ligation incubated at 15° C. for 20 hours. The ligation was diluted to promote circularization by the additions of ~ 48 μl. distilled water, 16 μl. 5X kinase/ligase buffer, 16 μl. 0.66 ATP and 1 μl. ligase. The solution was incubated for 72 hours at 15° C. and then the reaction terminated by raising the temperature to 70° C. for 10 minutes. The DNA was precipitated by adding 12 μl. 3M NaOAc and 300 μl. cold ethanol to each tube. The tube was incubated on dry ice for 10 minutes and then the DNA was collected in a Brinkman microfuge, washed once with 70% ethanol, air dried and finally resuspended in 30 μl. TE.

EXAMPLE 8

Isolation of Plasmid pHJL280 (An Alternative to Example 7)

A. Culture of *E. coli* K12 HB101/pHJL280

Lyophils of *E. coli* K12 HB101/pHJL280 can be obtained from the NRRL under the accession number NRRL B-18043. The lyophilized cells are streaked onto L-agar plates (L agar contains 10 gm. of Bacto Tryptone, 5 gm. of Bacto Yeast Extract, 10 gm. of NaCl, 2 gm. of glucose, and 15 gm. of agar per liter) containing 50 μg./ml. ampicillin to obtain a single-colony isolate of *E. coli* K12 HB101/pHJL280. One such colony was used to inoculate 100 ml. of LB medium (LB medium is L agar without the agar) and plasmid DNA was prepared as described in Example 6.

EXAMPLE 9

Construction of Plasmid pSKC16

A. BamHI Digestion of pHJL401

About 2 μg. of plasmid pHJL401 (described in Larson and Hershberger, 1986, Plasmid 15:199 and isolated and prepared, as described in Example 8, from Budapest Treaty deposit NRRL B-18217 (May 7, 1987) is mixed with 20 units of restriction enzyme BamHI in a total volume of 25 μl. of the BamHI buffer (100mM NaCl, 10mM Tris-HCl (pH 7.4), 10 mM MgCl₂ 10mM 2 mercaptoethanol) and 5 μl of 1 mg./ml. bovine serum albumin plus 2 μl. of 10 μ./μl. BamHI enzyme from New England Biolabs. The reaction is incubated at 37° C. for four hours, and then terminated by heating to 70° C. for 10 minutes. The restricted DNA is then maintained at 0° C. until use.

B. BamHI Digestion of pHJL280

About 5 μg. of pHJL280 DNA, prepared in substantial accordance with the teaching of Example 8, is mixed with 20 units of BamHI in a total volume of 50 μl. of the BamHI buffer (150mM NaCl, 6mM Tris-HCl (pH 7.9), 6mM MgCl₂ plus 5 μl. of 1 mg./ml. plus 2 μl. of 10 μ./μl. BamHI enzyme from New England Biolabs. The reaction is incubated at 37° C. for 4 hours, and terminated by heating at 70° C. for 10 minutes. The resulting BamHI fragments are separated by agarose gel electrophoresis, and the ~6 kb fragment containing the tylE, tylD, tylH, tylF and tylJ genes is isolated by standard procedures. The isolated fragment is maintained at 0° C.

C. Ligation of BamHI Digested pHJL401 with the ~ 6 kb BamHI Fragment Containing tylE, tylD, tylH, tylF, and tylJ The BamHI digested pHJL401 and the ~6 kb BamHI fragment of pHJL280 are mixed together and precipitated by addition of 0.1 volume of 3M NaOAc and 2.5 volumes of absolute ethanol. The precipitate is dissolved in 50 μl. ligase-kinase buffer (0.25M Tris-HCl, pH 7.8, 50mM MgCl₂, 25mM dithiothreitol and 25% glycerol). Twelve μl. of 0.66M ATP and two μl. of T4 DNA ligase are added and the solution is incubated at 15° C. for 18 hours.

D. Transformation of GS77

Figure 4:
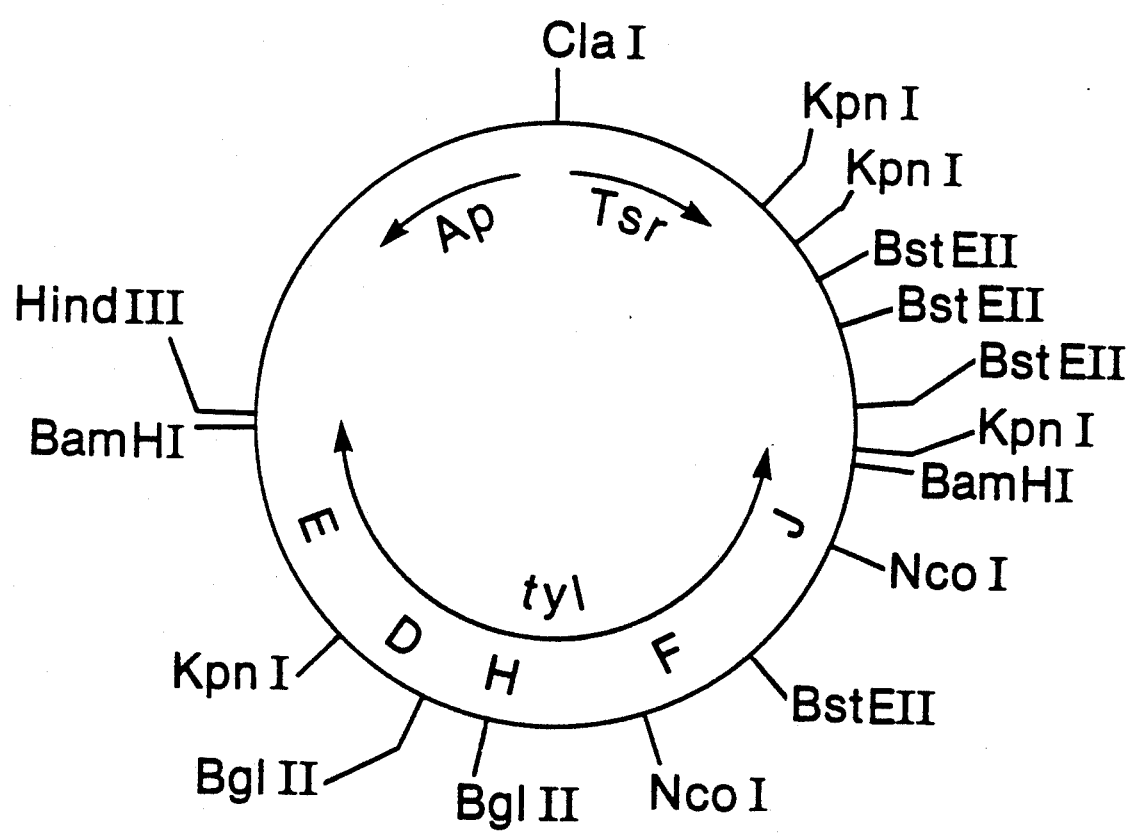
FIG. 4: Restriction Site and Function Map of Plasmid pSKC16

The ligation reaction is terminated by incubation at 70° C. for 10 minutes, and the DNA is precipitated by addition of 0.1 volume of 3M NaOAc and the 2.5 volume of absolute ethanol and maintained at −70° C. for 15 minutes. The precipitate, which contains the desired plasmid, pSKC16, is dissolved in 20 μl. of TE, and 10 μl. is used to transform GS77 in accordance with the procedure described in Example 10. Thiostrepton-resistant transformants are screened for production of 20-deoxotylosin, and plasmid DNA from these colonies is analyzed to confirm the correct plasmid structure. Two plasmids, pSKC16 and pSKC19, result from the procedure, differing in the orientation of the 6 kb BamHI fragment in pHJL401. A map of plasmid pSKC16, which can be conventionally identified and distinguished from plasmid pSKC19, is shown in FIG. 4 of the accompanying drawings.

EXAMPLE 10

Construction of *Streptomyces fradiae* GS77/pHJL280

The plasmid DNA, prepared as described in Example 7 or 8, can be transformed directly into GS77 but a more efficient method involves first amplifying the plasmid DNA and confirming its structure in *E. coli*. A large amount of the desired plasmids can then be purified from *E. coli* and used to transform the *Streptomyces fradiae* strains. The methods for introducing plasmid DNA into *E. coli* by transformation, identifying the plasmid by restriction enzyme analysis, and purifying large quantities of plasmid from *E. coli* are common and well known to those skilled in the art. The appropriate plasmids (i.e., those with the DNA inserts which were detected by hybridization to pSVB9, Example 5) are purified in substantial accordance with the teaching of Example 6, and about 5 μg. of each is transformed into GS77.

A culture of *Streptomyces fradiae* GS77 (ATCC 31733) was inoculated into 20 ml. of trypticase-soy broth (TSB) and incubated in a water-bath incubator at 29° C. at 260 rpm overnight (about 16 hours). The culture was homogenized using a homogenizing vessel (Thomas Scientific, Swedesboro, N.J.) and a T-Line laboratory stirrer and then fragmented using a Sonifier Cell Disruptor (Head Systems Ultrasonics, Inc.) for 7 seconds at 76 Watts. Four ml. of the homogenized, fragmented culture were inoculated into 20 ml. of TSB (BBL) containing 0.3% weight by volume glycine, and the culture was again incubated for 16-24 hours at 29° C. Then the culture was homogenized and recultured as described above. After this third 16-24 hour incubation, the culture was homogenized, collected, and then washed twice with P medium. P medium base was prepared by adding 103 gm. of sucrose to 0.25 gm. of K₂SO₄ and 2.03 gm. of MgCl₂.6H₂O and then adding deionized water to a final volume of 700 ml. The mixture was then sterilized, and to each 70 ml. of solution, about 10 ml. each of 0.05 gm. KH₂PO₄/100 ml. of deionized water; 2.78 gm. CaCl₂/100 ml. of deionized water; and 0.25 M TES (2-([tris-(hydroxymethyl)-methyl]amino)ethanesulfonic acid) at a pH=7.2 were added to form the desired P medium.

The cell pellet was resuspended in 15 ml. of P medium containing 1 mg./ml. lysozyme (Calbiochem, La Jolla, Calif. 92037) and then incubated at room temperature for about one and one-half hours to form protoplasts. The protoplasts were gently collected by centrifugation, washed twice with P medium, resuspended in 2 ml. of P medium, and incubated on ice until use. About 5 μg. of plasmid pHJL280 DNA was added to about 50 μl. of 1 mg./ml. heparin sulfate (Sigma) in P medium and incubated on ice for about 10 minutes. Much less plasmid DNA, about 5–100 nanograms, can be used to transform *Streptomyces fradiae* strains if such DNA is first replicated in a *S. fradiae* host rather than used directly from an *E. coli* strain. The procedure for isolating *Streptomyces* plasmid DNA is well known and also described in Hopwood et al., 1985, Genetic Manipulation of *Streptomyces: A Laboratory Manual* (John Innes Foundation, Norwich, England). The DNA/heparin solution was first added to about 200 μl. of protoplasts, and about 0.9 ml. of a solution composed of 55% PEG 1000 (Sigma) in P medium was then added to the DNA/protoplast mixture, and the resulting mixture was gently mixed at room temperature.

The mixture was plated in varying aliquots onto R2 plates using 4 ml. of soft R2 agar overlays. R2 plates contain 30 ml. of R2 media and have been dried at 37° C. for about 4 days. R2 medium is prepared by adding 103 gm. sucrose, 0.25 gm. $K_2SO_4$, 2 ml. of trace element solution, 10.12 gm. $MgCl_2.bH_2O$, 10.0 gm. glucose, 2.0 gm. of L-asparagine, 0.1 gm. of Casamino acids, and 22 gm. of agar to 700 ml. of water; sterilizing the resulting solution; and finally, adding 100 ml. of each of the following solutions: 0.05 gm. $KH_2PO_4$/100 ml. of deionized water; 2.22 gm. $CaCl_2$/100 ml. of deionized water; and 0.25 M TES, pH=7.2. The pH of the final solution is adjusted to equal 7.2 with NaOH. Trace element solution contains 40 mg. $ZnCl_2$, 200 mg. $FeCl_3.6H_2O$, 10 mg. $CuCl_2.2H_2O$, 10 mg. $MnCl_2.4H_2O$, 10 mg. $Na_2B_4O_7.10H_2O$, and 10 mg. $(NH_4)_6Mo_7O_{24}.4H_2O$ per liter. The soft R2 agar overlays are prepared by adding 51.5 gm. of sucrose, 5.06 gm. $MgCl_2.6H_2O$, 1.11 gm. $CaCl_2$, 50 ml. of 0.25 M TES at a pH=7.2, and 2.05 gm. agar to enough deionized water to achieve a final volume of 500 ml. The mixture is steamed to melt the agar, distributed into tubes (4 ml. each), and autoclaved prior to use. After the transformed protoplasts had been plated, the plates were incubated at 29° C. for 24 hours, and then, 4 ml. of soft R2 agar containing 25 μl. of 50 mg./ml. thiostrepton in dimethylsulfoxide (E. R. Squibb, Princeton, N.J. 08540) were spread over the protoplasts. Incubation of the plates at 29° C. was continued until regeneration was complete, usually a period of about 7–14 days, to select for the desired *Streptomyces fradiae* GS77/pHJL280 transformants. The *S. fradiae* GS77/pHJL280 strain was cultured under the fermentation conditions described in U.S. Pat. No. 4,419,447, which is incorporated by reference, except that the media were supplemented with 20 μg./ml. of thiostrepton to maintain the plasmid. 20-deoxotylosin production was conventionally assayed and determined in substantial accordance with the teaching of Baltz and Seno, 1981, *Antimicrobial Agents and Chemotherapy*, 20:214–225; and Kennedy, J. H., 1983, *Journal of Chromatography*, 281:288–292. The compound was identified initially by its co-chromatography with a known sample of 20-deoxotylosin. A known sample of 20-deoxotylosin may be obtained by following the teaching of Example 11.

EXAMPLE 11

Preparation and Use of 20-Deoxotylosin As A Standard For Identifying 20-Deoxotylosin A seven-day fermentation culture of *Streptomyces fradiae* GS77/pHJL280 is filtered through Whatman #1 filter paper. The filtrate is adjusted to pH 9 with 1N sodium hydroxide, and extracted with two volumes of ethyl acetate. The 20-deoxotylosin present in the ethyl acetate is concentrated 2–4 fold by evaporation. Approximately 10 μl. is applied to a silica gel thin layer chromatography plate. After the spot has dried, the plate is developed in a solvent consisting of 95% ethyl acetate and 5% diethylamine. After the plate has dried, 20-deoxotylosin can be visualized by either of two methods: (1) the plate is scanned for material absorbing at 280 nanometers using a Shimadzu CS930 plate scanner, or (2) the plate is dipped in a solution consisting of 3 gm. of Vanillin dissolved in 97 ml. of methanol and 3 ml. of concentrated sulfuric acid, and heated at 100° C. for 10–20 minutes: 20-Deoxotylosin appears as a blue spot under these conditions. 20-Deoxotylosin has an $R_f$ value of about 0.65 in this chromatography system. Unknown fermentation samples can be screened for 20-deoxotylosin using the thin layer chromatography system or HPLC and comparing the $R_f$ of the unknown compound(s) to that of the material prepared from *S. fradiae* GS77/pHJL280. 20-Deoxotylosin has the following physical characteristics:

U.V. (EtOH): $\lambda_{max}$282 nm (ε21400)

I.R. ($CHCl_3$, $cm^{-1}$): 3019, 2975, 2935, 2879, 1593, 1456, 1378, 1233, 1228, 1205, 1185, 1161, 1142, 1117, 996, 986

EXAMPLE 12

Construction of *Streptomyces rimosus* AB3 Double Mutant

Obtaining a double mutant in the tylosin bio-synthetic pathway of *Streptomyces rimosus* (ATCC 10970) is carried out by mutating with N-methyl-N'-nitro-N-nitrosoguanidine (MNNG) in substantial accordance with the teaching of Example 14. Double mutants involving the tylI and tylD biosynthetic genes can be conventionally identified and selected in accordance with the principles disclosed in Baltz and Seno (1981), in Antimicrobial Agents and Chemotherapy, 20:214–225. The two major tylosin-like macrolide antibiotics produced by the tylI, tylD mutant are 20-deoxy-20-dihydro-O-mycaminosyl tylonolide ($R_f$=0.39) and 20-deoxy-20-dihydrodemycinosyl tylosin ($R_f$=0.50). These $R_f$'s are determined using the thin layer chromatography system described in Example 11. The resultant strain is designated as *S. rimosus* AB3 and is useful as a host for purposes of the present invention.

EXAMPLE 13

Construction of *Streptomyces hygroscopicus* AB4 Double Mutant

The procedure for obtaining a double mutant in the tylosin biosynthetic pathway of *Streptomyces hygroscopicus* (ATCC 10976) is carried out in substantial accordance with the teaching of Example 12 except that *S. hygroscopicus* is used instead of *Streptomyces rimosus*. Double mutations involving the tylI and tylD biosynthetic genes can be conventionally identified and selected in substantial accordance with the teaching of Example 12. The resultant strain is designated as *S. hygroscopicus* AB4.

EXAMPLE 14

Generation and Identification of a Single tylII Mutant of *Streptomyces fradiae*

A preserved specimen of a tylosin producing strain of *Streptomyces fradiae* (e.g., ATCC 19609) is inoculated into 20 ml. of TSB and grown aerobically for 24–48 hours at 30° C. until well grown. The culture is homogenized and sonicated (see Example 19), and 5 ml. is inoculated into 45 ml. of TSB. The culture is grown aerobically for 16–24 hours, again fragmented, and 5 ml. aliquots are inoculated into 45 ml. of TSB in several replicate flasks. The cultures are grown for 2.5–3 hours aerobically at 37° C., the pH is adjusted to 8.5 with hydroxide, and then 25 μg./ml. of chloramphenicol and different amounts of N-methyl-N'-nitro-N-nitrosoguanidine (MNNG) are added to produce final concentrations of 100, 200, or 300 μg./ml. of MNNG. The cultures are grown for 20 minutes, samples are removed to test viability, and the remaining cells are pelleted by centrifugation and resuspended in fresh TSB. The cultures are grown for 16–24 hours at 37° C. The cultures which exhibit reasonably good growth after incubation are homogenized, sonicated, diluted in TSB and plated to obtain isolated mutagenized colonies on ASl medium (yeast extract, 1 gm./l.; L-alanine, 0.2 gm./l.; L-arginine, 0.2 gm./l.; L-asparagine, 0.5 gm./l.; soluble starch, 5 gm./l.; sodium chloride, 2.5 gm./l.; $Na_2SO_2$, 10 gm./l.; Meer agar, 20 gm./l; pH 7.5 before sterilizing). The plates are incubated for 7–14 days at 29°–30° C. to allow colony growth. Individual colonies are inoculated into small flasks or bottles containing 7–10 ml. of known tylosin fermentation medium (Baltz and Seno, *Antimicrobial Agents and Chemotherapy*, 20:214–225, 1981). A copy patch of each colony is simultaneously made on another ASl plate. The fermentation cultures are grown aerobically at 29° C. for 7 days and the individual fermentation broths are analyzed by thin layer chromatography for the presence of macrolide components as previously described (Baltz and Seno, 1981). 20-deoxotylosin can be initially identified by co-chromatography with known samples of 20-deoxotylosin (Example 11). The mutant (tylII) producing this compound is then preserved and used for production of 20-deoxotylosin.

EXAMPLE 15

Construction of *Streptomyces rimosus* AB3/pSKC16

The construction of *Streptomyces rimosus* AB3/pSKC16 is carried out in substantial accordance with the teaching of Example 10 except that a culture of *S. rimosus* AB3 and plasmid pSKC16 is used instead of *Streptomyces fradiae* GS77 and plasmid pHJL280. 20-deoxotylosin production is conventionally assayed and determined in substantial accordance with the teaching of Baltz and Seno, 1981, in Antimicrobial Agents and Chemotherapy 20:214–225; and Kennedy, J. H., 1983, Journal of Chromatography 281:288–292. The compound is identified initially by its co-chromatography with a known sample of 20-deoxotylosin (Example 11).

EXAMPLE 16

Construction of *Streptomyces hygroscopicus* AB4/pSKC16

The construction of *Streptomyces hygroscopicus* AB4/pSKC16 is carried out in substantial accordance with the teaching of Example 10 except that a culture of *S. hygroscopicus* AB4 and plasmid pSKC16 is used instead of *Streptomyces fradiae* GS77 and plasmid pHJL280. 20-deoxotylosin production is conventionally assayed and determined in substantial accordance with the teaching of Baltz and Seno, 1981, in *Antimicrobial Agents and Chemotherapy* 20:214–225; and Kennedy, J. H., 1983, Journal of Chromatography 281:288–292. The compound is identified initially by its co-chromatography with a known sample of 20-deoxotylosin (Example 11).

EXAMPLE 17

Construction of *Streptomyces rimosus* AB3/pSKC19

The construction of *Streptomyces rimosus* AB3/pSKC19 is carried out in substantial accordance with the teaching of Example 10 except that a culture of *S. rimosus* AB3 and plasmid pSKC19 is used instead of *Streptomyces fradiae* GS77 and plasmid pHJL280. 20-deoxotylosin production is conventionally assayed and determined in substantial accordance with the teaching of Baltz and Seno, 1981, in Antimicrobial Agents and Chemotherapy 20:214–225; and Kennedy, J. H., 1983, Journal of Chromatography 281:288–292. The compound is identified initially by its co-chromatography with a known sample of 20-deoxotylosin (Example 11).

EXAMPLE 18

Construction of *Streptomyces hygroscopicus* AB4/pSKC19

The construction of *Streptomyces hygroscopicus* AB4/pSKC19 is carried out in substantial accordance with the teaching of Example 10 except that a culture of *S. hygroscopicus* AB4 and plasmid pSKC19 is used instead of *Streptomyces fradiae* GS77 and plasmid pHJL280. 20-deoxotylosin production is conventionally assayed and determined in substantial accordance with the teaching of Baltz and Seno, 1981, in Antimicrobial Agents and Chemotherapy 20:214–225; and Kennedy, J. H., 1983, Journal of Chromatography 281:288–292. The compound is identified initially by its co-chromatography with a known sample of 20-deoxotylosin (Example 11).

EXAMPLE 19

Integration Of Plasmid pHJL280 Into The *Streptomyces Fradiae* GS77 Genome For Improved Production of 20-deoxotylosin GS77 is transformed with pHJL280 and thiostrepton-resistant transformants are selected as described in Example 10. A transformant, in which the presence of pHJL280 has been verified, is selected and inoculated into TSB plus thiostrepton (20 μg./ml.). The culture is shaken at 30° C. until fully grown (about 48 hours). The culture is homogenized in a glass homogenizer (Thomas Scientific, Swedesboro, N.J.) and fragmented by treatment with ultrasonic vibration (Heat Systems Ultrasonics, Inc.;1 cm probe; 7 seconds at 76 watts). Inoculum from this culture is then serially passaged 3 times in TSB without thiostrepton. After each passage, the culture is fragmented and inoculated at a level of 10% of volume. Following the final passage, the culture is fragmented and plated on ASI agar medium (see Example 14 for composition) containing thiostrepton. A thiostrepton resistant colony is picked and grown in TSB. When fully grown, the culture is fragmented and the plating efficiency on medium containing thiostrepton is determined. If the efficiency is at or near a value of 1.00, the pHJL280 plasmid has integrated into the genome, because the autonomous plasmid is unstable and is lost during growth in the absence of antibiotic selection. If the efficiency of plating is much less than 1.00, a thiostrepton resistant colony is picked and the growth in the absence of selection is repeated to again assess the efficiency of plating on thiostrepton. This procedure is repeated until an efficiency of plating equal to or near 1.00 is obtained, indicating that a culture containing pHJL280 integrated into the genome has been obtained. This culture is then used to produce 20-deoxotylosin by the method described in Example 10.

We claim:

1. A process for producing 20-deoxotylosin which comprises culturing a strain of *Streptomyces fradiae,* said strain:
   (a) comprising genes encoding enzymes of the tylosin antibiotic pathway; and
   (b) comprising one or more mutations that prevent the expression of the tylI gene.

2. A process of claim 1 wherein said strain:
   (a) comprises one or more mutations that prevent the expression of tylosin biosynthetic genes tylI and R, in which R is one or more tylosin biosynthetic genes selected from the group consisting of tylA, tylB, tylL, tylM, tylH, tylD, tylJ, tylG, tylK, tylC, tylE, and tylF; and,
   (b) is transformed with a recombinant DNA cloning vector which comprises DNA which complements said mutation or mutations in R thereby allowing for expression of R;
   said culture conditions suitable for cell growth, expression of R and production of 20-deoxotylosin.

3. The process of claim 2 wherein said recombinant DNA cloning vector is maintained during the culturing step as an autonomously replicating vector.

4. The process of claim 3 wherein the recombinant DNA cloning vector is a plasmid.

5. The process of claim 4 wherein the plasmid is plasmid pHJL280, pSKC16, or pSKC19.

6. The process of claim 5 wherein said recombinant DNA cloning vector is maintained during the culturing step as a sequence integrated into the genomic DNA of said microorganism.

7. The process of claim 2 wherein the DNA which complements said mutation or mutations in R is maintained during the culturing step by integration into the genomic DNA of said microorganism.

8. A process as claimed in claim 2 in which a mutant complementing DNA sequence is a sequence encoding the tylD product.

9. The process of claim 8 wherein the tylI mutant strain is *Streptomyces fradiae* GS77.

* * * * *